(12) United States Patent
Walters

(10) Patent No.: US 9,107,760 B2
(45) Date of Patent: Aug. 18, 2015

(54) STAND ALONE INTERBODY FIXATION SYSTEM

(75) Inventor: Carmen Walters, Carlsbad, CA (US)

(73) Assignee: ALPHATEC SPINE, INC, Carlsbad, CA (US)

(*) Notice: Subject to any disclaimer, the term of this patent is extended or adjusted under 35 U.S.C. 154(b) by 18 days.

(21) Appl. No.: 13/453,054

(22) Filed: Apr. 23, 2012

(65) Prior Publication Data

US 2012/0277868 A1 Nov. 1, 2012

Related U.S. Application Data

(60) Provisional application No. 61/479,206, filed on Apr. 26, 2011.

(51) Int. Cl.
*A61F 2/44* (2006.01)
*A61F 2/28* (2006.01)
*A61F 2/30* (2006.01)

(52) U.S. Cl.
CPC .............. *A61F 2/442* (2013.01); *A61F 2/447* (2013.01); *A61F 2002/2835* (2013.01); *A61F 2002/3038* (2013.01); *A61F 2002/30289* (2013.01); *A61F 2002/30365* (2013.01); *A61F 2002/30367* (2013.01); *A61F 2002/30382* (2013.01); *A61F 2002/30504* (2013.01); *A61F 2002/30738* (2013.01); *A61F 2002/30787* (2013.01); *A61F 2002/30827* (2013.01); *A61F 2002/30845* (2013.01); *A61F 2002/30919* (2013.01); *A61F 2002/4475* (2013.01)

(58) Field of Classification Search
USPC ............................................ 623/17.11–17.16
See application file for complete search history.

(56) References Cited

U.S. PATENT DOCUMENTS

| | | | | |
|---|---|---|---|---|
| 5,683,394 A | * | 11/1997 | Rinner | 606/86 R |
| 6,770,096 B2 | * | 8/2004 | Bolger et al. | 623/17.16 |
| 2009/0054988 A1 | * | 2/2009 | Hess | 623/17.16 |
| 2011/0035007 A1 | * | 2/2011 | Patel et al. | 623/17.11 |
| 2011/0118840 A1 | * | 5/2011 | Huntsman et al. | 623/17.11 |
| 2011/0208311 A1 | * | 8/2011 | Janowski | 623/17.16 |

* cited by examiner

*Primary Examiner* — Kevin T Truong
*Assistant Examiner* — Tracy Kamikawa
(74) *Attorney, Agent, or Firm* — Michael J. Loi

(57) ABSTRACT

An interbody spacer system includes a cage and at least one first fixation blade. The cage includes an anterior wall and a posterior wall connected by a pair of side walls. The at least one first fixation blade partially extends around an outer surface of a first of the pair of side walls and is positionable between a first configuration for insertion into a disk space between two vertebrae and a second configuration for attachment to a first of the vertebrae.

8 Claims, 5 Drawing Sheets

STAND ALONE INTERBODY FIXATION SYSTEM

CROSS-REFERENCE TO RELATED APPLICATIONS

The present application claims priority to U.S. Provisional Application 61/479,206, filed Apr. 26, 2011.

FIELD

The present disclosure relates generally to spinal fusion devices. More specifically, example embodiments are directed to a stand alone interbody spacer.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

The spine is a flexible column formed of a plurality of bones called vertebrae. The vertebrae include a hollow cavity and essentially stack one upon the other, forming a strong column for support of the cranium and trunk of the body. The hollow core of the spine houses and protects the nerves of the spinal cord. The different vertebrae are connected to one another by means of articular processes and intervertebral, fibrocartilaginous bodies. Each vertebra includes upper and lower endplates formed from harder compact bone than the softer cancellous bone of the interior of the vertebra.

The intervertebral bodies, also known as intervertebral discs, include a fibrous ring filled with pulpy material. The discs function as spinal shock absorbers and also cooperate with synovial joints to facilitate movement and maintain flexibility of the spine. When one or more discs degenerate through accident or disease, nerves passing near the affected area may be compressed and consequently irritated. The result may be chronic and/or debilitating neck and/or back pain due to these spinal disorders.

Various methods and apparatus have been designed to relieve such back pain, including spinal fusion using an interbody spacer and suitable graft using techniques such as anterior interbody fusion, posterior interbody fusion, or transforaminal interbody fusion surgical techniques. The implants used in-these techniques are placed in the intervertebral disc space between adjacent vertebrae of the spine. Bone graft material may be placed within the spacers to facilitate bone growth between the adjacent vertebrae. Many times an exterior plate and/or screws are used in conjunction with the implant to hold the adjacent vertebrae while the fusion occurs.

Ideally, the interbody spacer should stabilize the intervertebral space and allow fusion of the adjacent vertebrae. Moreover, during the time it takes for fusion to occur, the interbody spacer should have sufficient structural integrity to withstand the stress of maintaining the space without substantially degrading or deforming and have sufficient stability to remain securely in place prior to actual bone in-growth fusion.

One significant challenge to providing fusion stability (prior to actual bone ingrowth fusion) is preventing spinal extension during patient movement. Distraction of the vertebral space containing the fusion graft may cause the interbody spacer to shift or move disrupting bone ingrowth fusion and causing pain. An exterior plate is often used with the interbody spacer to hold the adjacent vertebrae while the fusion occurs. There remains a need for an interbody spacer capable of holding the adjacent vertebrae steady during fusion without the use of external plates.

SUMMARY

An interbody spacer system includes a cage and at least one first fixation blade. The cage includes an anterior wall and a posterior wall connected by a pair of side walls. The at least one first fixation blade partially extends around an outer surface of a first of the pair of side walls and is positionable between a first configuration for insertion into a disk space between two vertebrae and a second configuration for attachment to a first of the vertebrae.

In other features, the system includes a shaft extending through a portion of the cage and coupled to the first fixation blade. The shaft rotates the first fixation blade from the first configuration to the second configuration. A second fixation blade partially extends around an outer surface of a second of the pair of side walls, positionable between the first configuration for insertion into the disk space and a second configuration for attachment to a second of the vertebrae. A recessed portion of the first side wall receives the first fixation blade in the first configuration. The first fixation blade and outer surface of the first side wall are flush in the first configuration.

DETAILED DESCRIPTION

Figure 1:
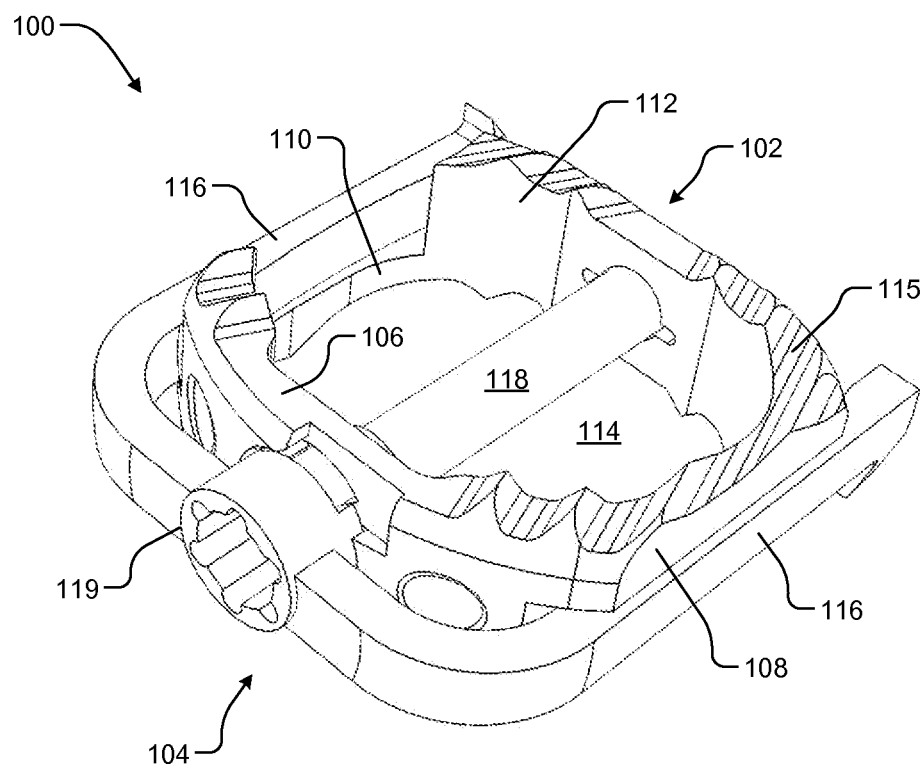
FIG. 1 is a top perspective view of an exemplary stand alone interbody spacer according to the principles of the present disclosure.
Figure 2:
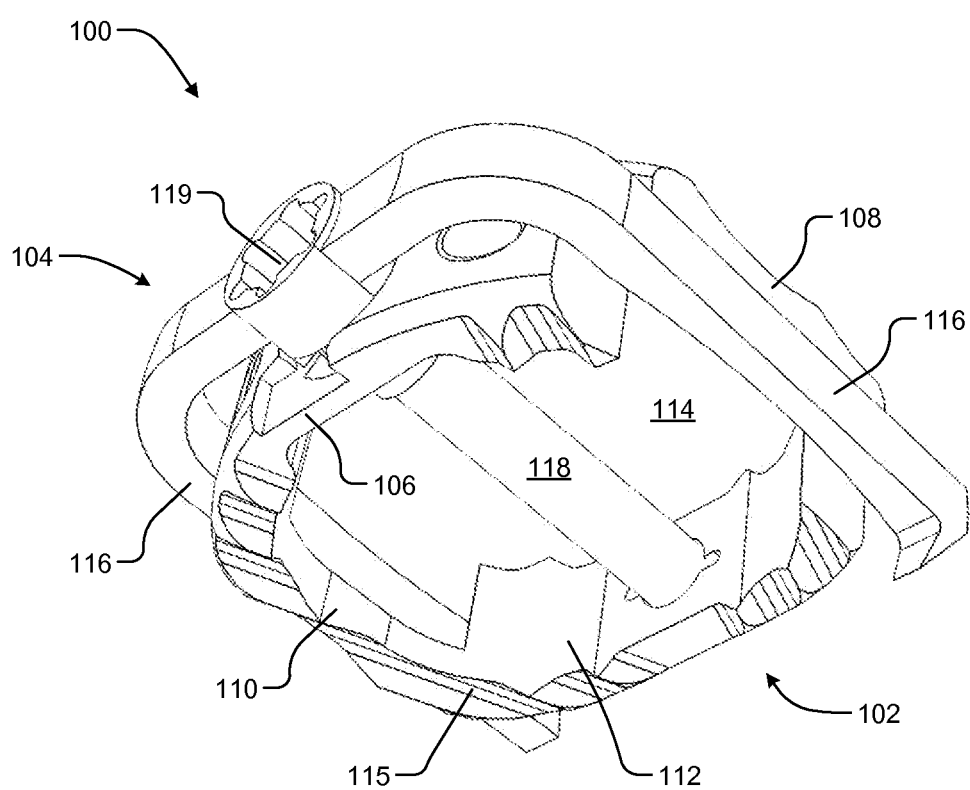
FIG. 2 is a bottom perspective view of the stand alone interbody spacer of FIG. 1 according to the principles of the present disclosure.
Figure 3:
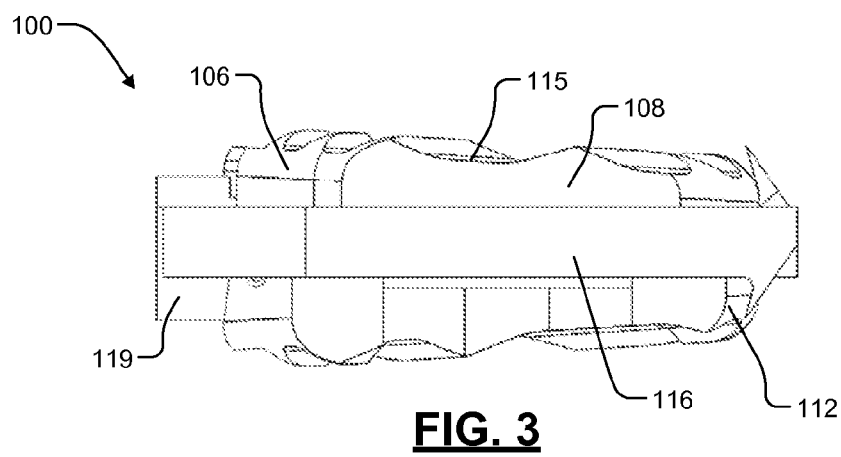
FIG. 3 is a lateral side view of the stand alone interbody spacer of FIG. 1 according to the principles of the present disclosure.
Figure 4:
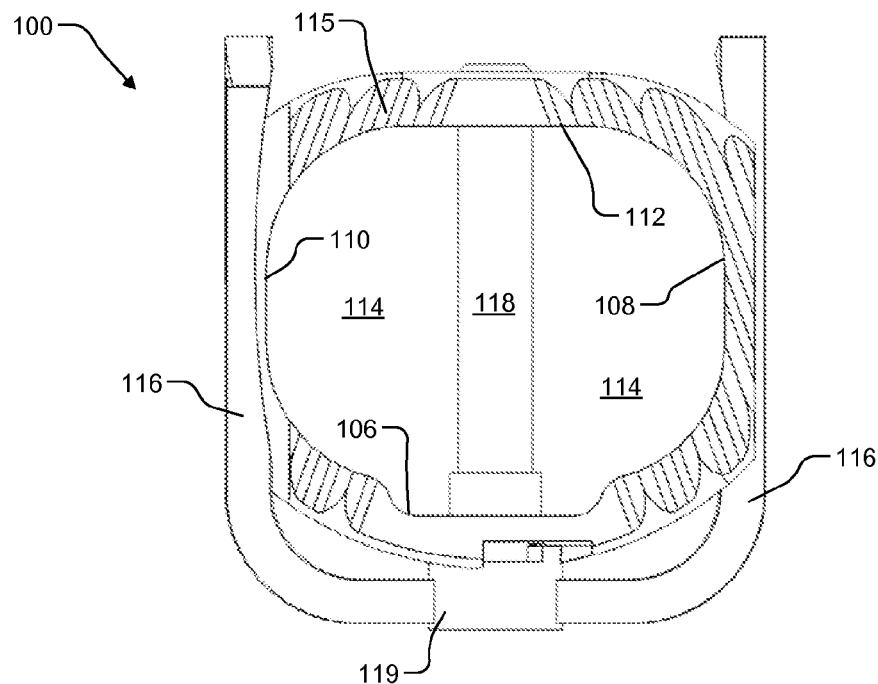
FIG. 4 is a top view of the stand alone interbody spacer of FIG. 1 according to the principles of the present disclosure.
Figure 5:
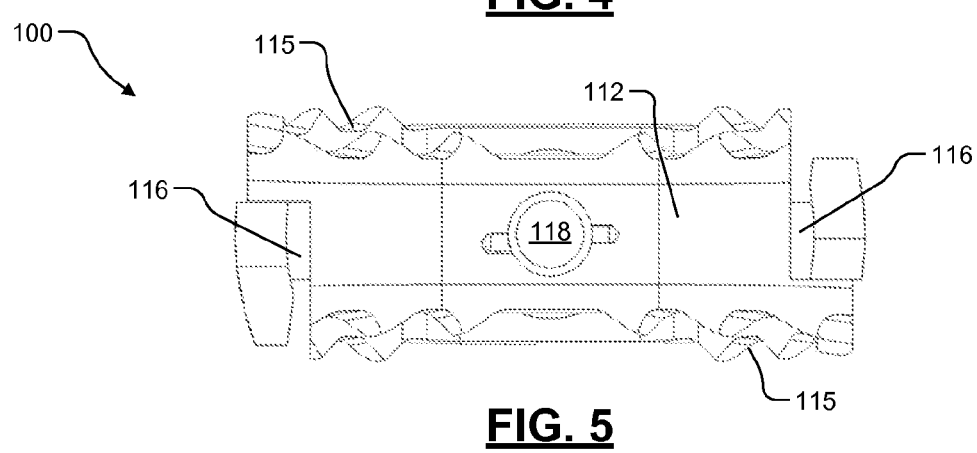
FIG. 5 is a posterior side view of the stand alone interbody spacer of FIG. 1 according to the principles of the present disclosure.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical "or." It should be understood that steps within a method may be executed in different order without altering the principles of the present disclosure.

Embodiments of the invention will now be described with reference to the Figures, wherein like numerals reflect like elements throughout. Embodiments of the invention may include several novel features, no single one of which is solely responsible for its desirable attributes or which is essential to practicing the invention described herein. The words proximal and distal are applied herein to denote specific ends of components of the instrument described herein. For example only, a proximal end refers to the end of an instrument nearer to an operator of the instrument when the instrument is being used. A distal end refers to the end of a component further from the operator and extending towards the surgical area of a patient and/or the implant. Similarly, the words left and right, top and bottom, and upper and lower may denote opposite sides of a component.

Referring now to FIGS. 1-6, an exemplary stand alone interbody fixation system 100 for spinal surgeries includes a cage 102 and an attachment member 104. The cage 102 may include a substantially annular shape formed by an anterior wall 106, lateral walls 108 and 110, and a posterior wall 112 that form a substantially hollow interior 114. A plurality of grooves 115 on upper and lower surfaces of the cage 102 may improve attachment of the cage 102 to the vertebrae. The attachment member 104 may include one or more fixation blades 116a-b (collectively blades 116) coupled to a shaft 118 at a hub 119. The shaft 118 may extend through into at least one of the walls 106-112. For example, in the present example, the shaft 118 extends through the anterior wall 106, a portion of the hollow interior 114, and into the posterior wall 112. One or more of the blades 116 may be positioned exterior to the walls 106-112. The blades 116 may rotate about the shaft 118 to engage vertebrae above and below the cage 102.

Other typical stand alone interbody fixation systems may include interior blades within the hollow interior of a cage. Because these interior blades must fit within the hollow interior of the cage, the dimensions must be limited to the dimensions of the interior sides of the various walls comprising the cage. Further, because the interior blades fill a portion of the hollow interior, less volume is available for packing of bone graft material.

The exterior blades 116 provide a larger radius of travel or arc length than prior stand alone interbody spacer systems having blades that deploy from the hollow interior 114. For example, in the cervical region of the spine, vertebrae and intervertebral disc space are substantially smaller than in lower regions of the spine. Therefore, spacers with internal blades are substantially limited in terms of arc length and engagement with the adjacent vertebrae. By positioning the blades external to the spacer/cage, the blades may include radial lengths greater than internal blades. Although the exterior blades 116 of the present example are substantially formed in right angles, other blade configurations may include curved blades, helical blades, and additional toothed and spiked blades.

Figure 6:
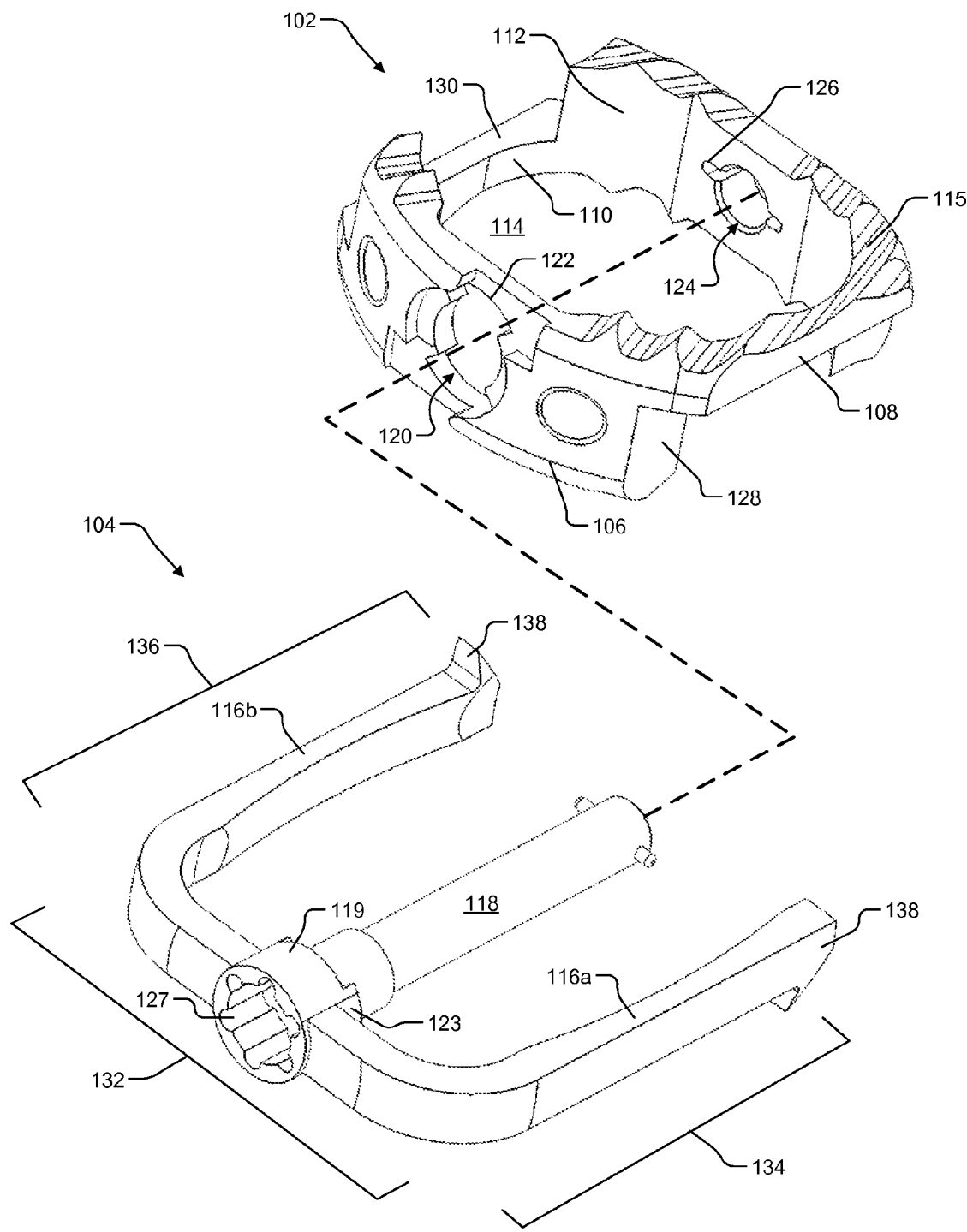
FIG. 6 is an exploded perspective view of the stand alone interbody spacer of FIG. 1 according to the principles of the present disclosure.

FIG. 6 illustrates an exploded perspective view of the system 100 showing additional features for coupling the cage 102 and the attachment member 104. The anterior wall 106 of the cage 102 may include an anterior aperture 120. The anterior aperture 120 may also include a keyed portion 122 that engages portions of the shaft 118 to lock the system 100 in one or more configurations. For example, the hub 119 may include posterior projections 123 configured to snap into the keyed portion 122. The posterior wall 112 of the cage may include a posterior aperture 124. The posterior aperture 124 may include a slot 126 for guiding the shaft 118 through the posterior wall 112. The attachment member 104 may be rotated from a non-deployed first configuration to a deployed second configuration by rotating the shaft 118 as illustrated in FIGS. 7A-7C and 8A-8C. For example, a deployment instrument (not shown) may engage a driving feature 127 of the hub 119.

The cage 102 may include nesting features for receiving the attachment member 104 within portions of the walls 106-112 in the first configuration. For example, in FIG. 6, the side walls 108 and 110 include recessed portions 128 and 130 configured to partially engage the attachment member 104. The blades 116 of the attachment member 104 may comprise an anterior member 132 extending substantially parallel with the anterior wall 106 and including the hub 119. A first arm 134 may extend posteriorly from the anterior member 132 and proximate to the first side wall 108 to form the first blade 116a. A second arm 136 may extend posteriorly from the anterior member 132 and proximate to the second side wall 110 to form the second blade 116b. First recessed portion 128 may permit nesting of the first arm 134 such that the outer surfaces of the first arm 134 and the side wall 108 are substantially flush with one another. Likewise, second recessed portion 130 may permit nesting of the second arm 136 such that the outer surfaces of the second arm 136 and the side wall 110 are flush with one another. Thus, the attachment member 104 may form a substantially unitary, U-shaped construction that surrounds the cage 102. Posterior ends of the blades 116 may include piercing members 138 such as spikes, claws, and the like for piercing the endplates of the vertebrae.

Figure 7A:
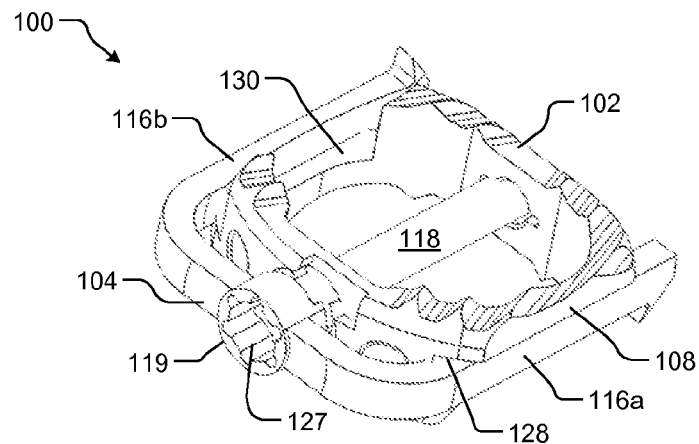
FIGS. 7A-7C are perspective views illustrating deployment of a fixation blade of the stand alone interbody spacer of FIG. 1.
Figure 7B:
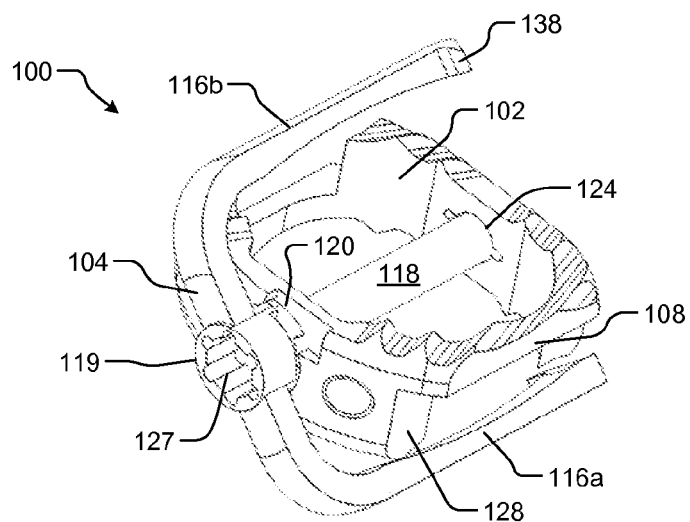
Figure 7C:
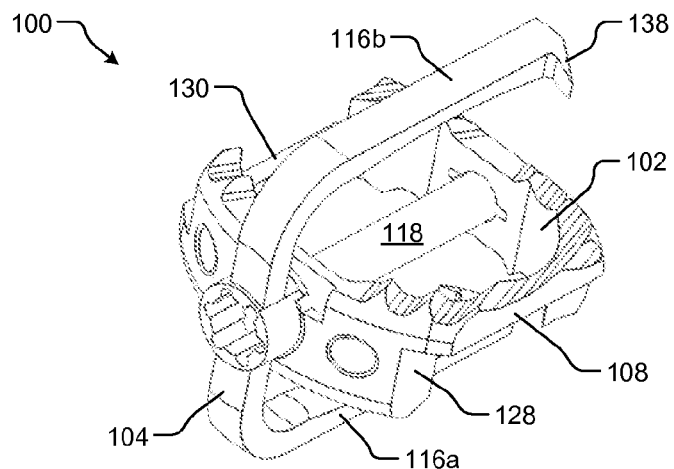
Figure 8A:
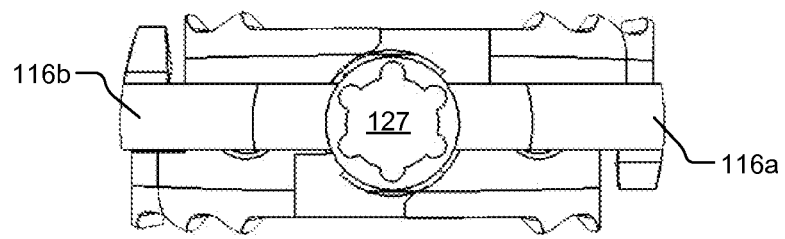
FIGS. 8A-8C are anterior side views illustrating deployment of a fixation blade of the stand alone interbody spacer of FIG. 1.
Figure 8B:
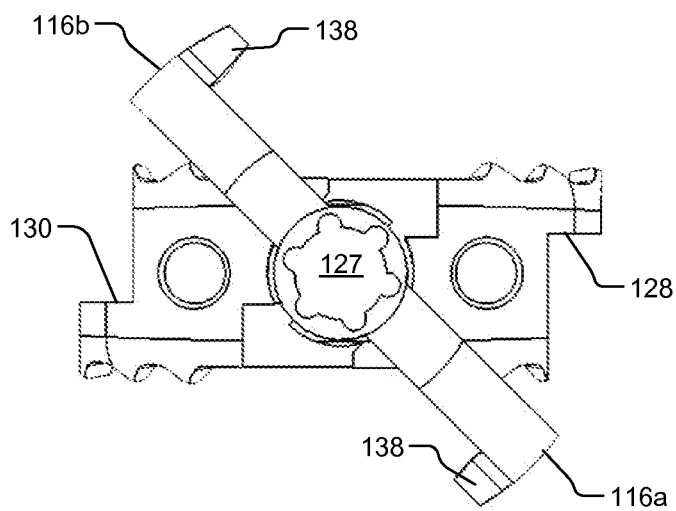

Referring now to FIGS. 7A-7C and 8A-8C, the system 100 may be deployed by rotating the shaft 118 within the cage 102. In FIGS. 7A and 8A, the system 100 is in a first non-deployed configuration with the first and second arms 134 and 136 nesting within the first and second recessed portions 128 and 130 respectively. The system 100 includes a slim profile for insertion into the intervertebral space. The deployment instrument (not shown) may engage the recess 127 of the hub 119 and apply a torque to rotate the attachment member 104 and deploy the system 100. As the shaft 118 rotates within the apertures 120 and 124 in FIGS. 7B and 8B, the first arm 134 may disengage the first recessed portion 128 and the second arm 136 may disengage the second recessed portion 130.

Figure 8C:
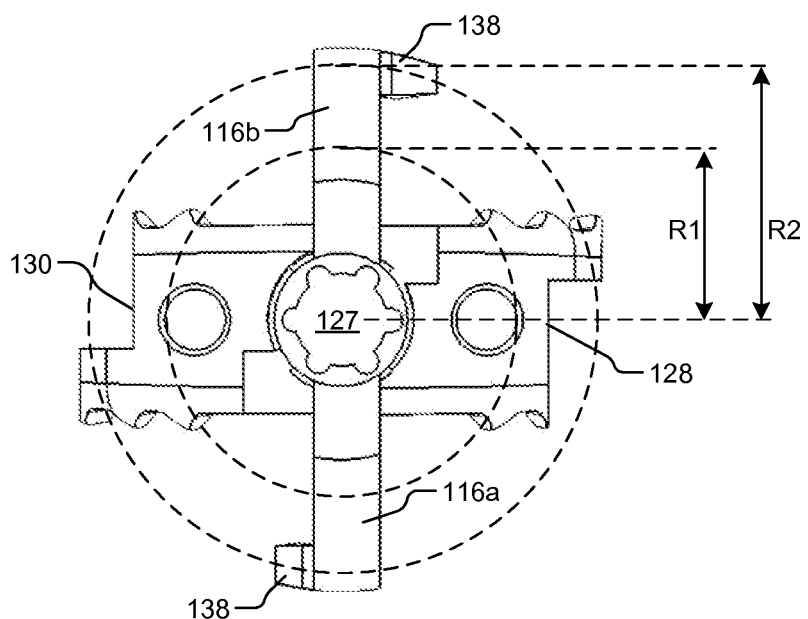

Rotation of the arms 134 and 136 positions the piercing members 138 closer to the endplates and begins engage the piercing members 138 with the endplates of the vertebrae. In FIGS. 7C and 8C, the system 100 is in a fully deployed configuration with the first and second arms 134 and 136 fully rotated and disposed at right angles relative to the cage 102. The piercing members 138 may fully engage the endplates of the vertebrae. The exterior fixation blades 116 may include a radius R1 of extension away from the shaft 118 that is greater than a radius R2 of typical interior blades of the prior art. The larger radius R1 provides greater encroachment and engagement within the endplates of the vertebrae. Exterior blades also provide increased volume within the hollow interior 114 of the cage 102.

Including blades that are exterior to the cage may present additional concerns regarding safety of the surgeon while handling the system 100. The system 100 may further comprise sterile packaging conducive to both transport and loading into the insertion/deployment tools. The tools themselves may include a protective sheath, sleeve, or outer members that surround the system 100 to prevent contact with the exterior blades 116.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents. The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

The invention claimed is:

1. An interbody spacer system, comprising:
    a cage including an anterior wall and a posterior wall connected by a pair of side walls, wherein the anterior wall includes an anterior aperture and the posterior wall includes a posterior aperture, and wherein a first of the pair of side walls includes a first recessed portion and a second of the pair of side walls includes a second recessed portion;
    a first fixation blade positionable between a first configuration for insertion into a disk space between two vertebrae and a second configuration for attachment to a first of the vertebrae;
    a second fixation blade positionable between the first configuration for insertion into the disk space and the second configuration for attachment to a second of the vertebrae; and
    a shaft extending through a portion of the cage and coupled to the first and second fixation blades to rotate the first and second fixation blades from the first configuration to the second configuration,
    wherein the anterior aperture and the posterior aperture are configured to receive the shaft,
    wherein the first recessed portion receives the first fixation blade in the first configuration, wherein the first fixation blade and an outer surface of the first of the pair of side walls are flush in the first configuration,
    wherein the second recessed portion receives the second fixation blade in the first configuration, wherein the second fixation blade and an outer surface of the second of the pair of side walls are flush in the first configuration, and
    wherein the first fixation blade partially extends around and is external to the first of the pair of side walls in the first configuration and the second fixation blade partially extends around and is external to the second of the pair of side walls in the first configuration.

2. The interbody spacer system of claim 1, wherein the shaft further comprises a hub having a driving feature for receiving a deployment instrument to rotate the shaft.

3. The interbody spacer system of claim 1, further comprising an anterior member extending substantially parallel to the anterior wall in the first configuration and coupling the first and second fixation blades with the shaft.

4. The interbody spacer system of claim 1, further comprising projections on the shaft to engage a keyed portion of the anterior aperture to lock the first and second fixation blades in the second configuration.

5. The interbody spacer system of claim 1, wherein the anterior, posterior, and side walls form a substantially annular shape including a hollow interior.

6. The interbody spacer system of claim 1, further comprising a plurality of grooves on upper and lower surfaces of the cage.

7. The interbody spacer system of claim 1, wherein the first and second fixation blades each include at least one piercing member for piercing endplates of the vertebrae.

8. The interbody spacer of claim 7, wherein the at least one piercing member comprises one of a spike and a claw.

* * * * *